(12) United States Patent
Marino et al.

(10) Patent No.: US 8,298,268 B2
(45) Date of Patent: Oct. 30, 2012

(54) MONO-PLANAR PEDICLE SCREW METHOD, SYSTEM AND KIT

(75) Inventors: James Marino, La Jolla, CA (US); Jamil Elbanna, San Diego, CA (US)

(73) Assignee: Trinty Orthopedics, LLC., San Diego, CA (US)

( * ) Notice: Subject to any disclaimer, the term of this patent is extended or adjusted under 35 U.S.C. 154(b) by 0 days.

(21) Appl. No.: 12/848,027

(22) Filed: Jul. 30, 2010

(65) Prior Publication Data

US 2010/0298890 A1 Nov. 25, 2010

Related U.S. Application Data

(63) Continuation of application No. 11/916,277, filed as application No. PCT/US2006/016042 on Apr. 27, 2006, now Pat. No. 7,780,706.

(60) Provisional application No. 60/675,742, filed on Apr. 27, 2005.

(51) Int. Cl.
*A61B 17/70* (2006.01)
(52) U.S. Cl. ...................................................... 606/264
(58) Field of Classification Search .......... 606/246–279; 403/76, 93, 96, 97
See application file for complete search history.

(56) References Cited

U.S. PATENT DOCUMENTS

| | | |
|---|---|---|
| 4,519,100 A | 5/1985 | Wills et al. |
| 4,827,918 A | 5/1989 | Olerud |
| 4,862,883 A | 9/1989 | Freeland |
| 4,987,892 A | 1/1991 | Krag et al. |
| 5,034,011 A | 7/1991 | Howland |
| 5,057,109 A | 10/1991 | Olerud |
| 5,190,543 A | 3/1993 | Schlapfer |
| 5,261,909 A | 11/1993 | Sutterlin et al. |
| 5,300,074 A | 4/1994 | Frigg |
| 5,308,327 A | 5/1994 | Heaven et al. |
| 5,312,402 A | 5/1994 | Schlapfer et al. |
| 5,423,826 A | 6/1995 | Coates et al. |
| 5,468,241 A | 11/1995 | Metz-Stavenhagen et al. |
| 5,476,464 A | 12/1995 | Metz-Stavenhagen et al. |
| 5,499,983 A | 3/1996 | Hughes |
| 5,536,268 A | 7/1996 | Griss |
| 5,571,105 A | 11/1996 | Gundolf |

(Continued)

FOREIGN PATENT DOCUMENTS

FR 2 855 392 * 3/2004

(Continued)

*Primary Examiner* — Eduardo C Robert
*Assistant Examiner* — Summer Kostelnik
(74) *Attorney, Agent, or Firm* — Fred C. Hernandez; Mintz, Levin, Cohn, Ferris, Glovsky and Popeo, P.C.

(57) ABSTRACT

A pedicle screw assembly (10) that includes a cannulated pedicle screw (20) having a scalloped shank (24), a swivel top head 30 having inclined female threads (44) in a left and right arm (34, 36) to prevent splaying, a set screw (50) having mating male threads 52, a rod conforming washer (60) that is rotatably coupled to the set screw (50), the conforming washer including reduced ends to induce a coupled rod (80) to bend. A rod reduction system including an inner and an outer cannula (90, 100), the inner cannula (90) including a left and right arm (92, 94) that engage the swivel top head's (30) left and right arm (34, 36) and the outer cannula (100) dimensioned to securely slide over the inner cannula (90) to reduce the rod (80) into the swivel top head's (30) rod receiving area (38).

20 Claims, 16 Drawing Sheets

U.S. PATENT DOCUMENTS

| | | |
|---|---|---|
| 5,616,143 A | 4/1997 | Schlapfer et al. |
| 5,643,264 A | 7/1997 | Sherman et al. |
| 5,645,544 A | 7/1997 | Tai et al. |
| 5,649,926 A | 7/1997 | Howland |
| 5,672,176 A | 9/1997 | Biedermann et al. |
| 5,702,397 A | 12/1997 | Goble et al. |
| 5,707,371 A | 1/1998 | Metz-Stavenhagen |
| 5,782,833 A | 7/1998 | Haider |
| 5,797,911 A | 8/1998 | Sherman et al. |
| 5,876,403 A | 3/1999 | Shitoto |
| 5,879,350 A | 3/1999 | Sherman et al. |
| 5,885,286 A | 3/1999 | Sherman et al. |
| 5,891,145 A | 4/1999 | Morrison et al. |
| 5,941,879 A | 8/1999 | Walulik et al. |
| 5,976,136 A | 11/1999 | Bailey et al. |
| 5,980,557 A | 11/1999 | Iserin et al. |
| 5,989,250 A | 11/1999 | Wagner et al. |
| 6,030,389 A | 2/2000 | Wagner et al. |
| 6,056,755 A | 5/2000 | Horas et al. |
| 6,123,706 A | 9/2000 | Lange |
| 6,132,430 A | 10/2000 | Wagner |
| 6,155,756 A | 12/2000 | Mericle et al. |
| 6,179,838 B1 | 1/2001 | Fiz |
| 6,214,004 B1 | 4/2001 | Coker |
| 6,224,600 B1 | 5/2001 | Protogirou |
| 6,254,602 B1 | 7/2001 | Justis |
| 6,280,442 B1 | 8/2001 | Barker et al. |
| 6,309,391 B1 | 10/2001 | Crandall et al. |
| 6,331,179 B1 | 12/2001 | Freid et al. |
| 6,355,036 B1 | 3/2002 | Nakajima |
| 6,368,321 B1 | 4/2002 | Jackson |
| 6,416,515 B1 | 7/2002 | Wagner |
| 6,440,133 B1 | 8/2002 | Beale et al. |
| 6,454,769 B2 | 9/2002 | Wagner et al. |
| 6,454,773 B1 | 9/2002 | Sherman et al. |
| 6,478,798 B1 | 11/2002 | Howland |
| 6,485,494 B1 | 11/2002 | Haider |
| 6,485,518 B1 | 11/2002 | Cornwall et al. |
| 6,488,681 B2 | 12/2002 | Martin et al. |
| 6,508,818 B2 | 1/2003 | Steiner et al. |
| 6,527,772 B2 | 3/2003 | Enayati |
| 6,530,929 B1 | 3/2003 | Justis et al. |
| 6,537,276 B2 | 3/2003 | Metz-Stavenhagen |
| 6,554,831 B1 | 4/2003 | Rivard et al. |
| 6,554,834 B1 | 4/2003 | Crozet et al. |
| 6,558,386 B1 | 5/2003 | Cragg |
| 6,565,565 B1 | 5/2003 | Yuan et al. |
| 6,575,979 B1 | 6/2003 | Cragg |
| 6,595,992 B1 | 7/2003 | Wagner et al. |
| 6,623,487 B1 | 9/2003 | Goshert |
| 6,626,908 B2 | 9/2003 | Cooper et al. |
| 6,641,586 B2 | 11/2003 | Varieur |
| 6,648,888 B1 | 11/2003 | Shluzas |
| 6,660,006 B2 | 12/2003 | Markworth et al. |
| 6,663,632 B1 | 12/2003 | Frigg |
| 6,679,883 B2 | 1/2004 | Hawkes et al. |
| 6,682,529 B2 | 1/2004 | Stahurski |
| 6,685,708 B2 | 2/2004 | Monassevitch et al. |
| 6,689,133 B2 | 2/2004 | Morrison et al. |
| 6,695,846 B2 | 2/2004 | Richelsoph et al. |
| 6,699,249 B2 | 3/2004 | Schlapfer et al. |
| 6,699,250 B1 | 3/2004 | Osterle et al. |
| 6,709,434 B1 | 3/2004 | Gournay et al. |
| 6,755,828 B2 | 6/2004 | Shevtsov et al. |
| 6,755,836 B1 | 6/2004 | Lewis |
| 6,770,075 B2 | 8/2004 | Howland |
| 6,790,209 B2 | 9/2004 | Beale et al. |
| 6,800,079 B2 | 10/2004 | Reed |
| 6,833,005 B1 | 12/2004 | Mantas et al. |
| 6,843,791 B2 | 1/2005 | Serhan |
| 6,902,565 B2 | 6/2005 | Berger et al. |
| 6,964,666 B2 | 11/2005 | Jackson |
| 6,974,460 B2 | 12/2005 | Carbone et al. |
| 7,011,685 B2 | 3/2006 | Arnin et al. |
| 7,087,058 B2 | 8/2006 | Cragg |
| 7,160,300 B2 | 1/2007 | Jackson |
| 7,166,109 B2 | 1/2007 | Biedermann et al. |
| 7,179,261 B2 | 2/2007 | Sicvol et al. |
| 7,186,255 B2 | 3/2007 | Baynham et al. |
| 7,201,753 B2 | 4/2007 | Schlapfer et al. |
| 7,220,262 B1 | 5/2007 | Hynes |
| 7,322,979 B2 | 1/2008 | Crandall et al. |
| 7,377,923 B2 | 5/2008 | Purcell et al. |
| 7,588,593 B2 | 9/2009 | Aferzon |
| 7,611,518 B2 | 11/2009 | Walder et al. |
| 7,850,718 B2 * | 12/2010 | Bette et al. .................. 606/267 |
| 2001/0007941 A1 | 7/2001 | Steiner et al. |
| 2001/0014807 A1 | 8/2001 | Wagner et al. |
| 2001/0021851 A1 | 9/2001 | Eberlein et al. |
| 2001/0025181 A1 | 9/2001 | Freedlan |
| 2001/0029376 A1 | 10/2001 | Sater et al. |
| 2001/0034521 A1 | 10/2001 | Bailey et al. |
| 2002/0010467 A1 | 1/2002 | Cooper et al. |
| 2002/0035366 A1 | 3/2002 | Walder et al. |
| 2002/0045898 A1 | 4/2002 | Freid et al. |
| 2002/0055741 A1 | 5/2002 | Schlapfer et al. |
| 2002/0058939 A1 | 5/2002 | Wagner et al. |
| 2002/0072749 A1 | 6/2002 | Enayati |
| 2002/0082599 A1 | 6/2002 | Crandall et al. |
| 2002/0091386 A1 | 7/2002 | Martin et al. |
| 2002/0120268 A1 | 8/2002 | Berger |
| 2002/0173789 A1 | 11/2002 | Howland |
| 2002/0173791 A1 | 11/2002 | Howland |
| 2003/0009168 A1 | 1/2003 | Beale et al. |
| 2003/0055426 A1 | 3/2003 | Carbone et al. |
| 2003/0060826 A1 | 3/2003 | Foley et al. |
| 2003/0083658 A1 | 5/2003 | Hawkes et al. |
| 2003/0105460 A1 | 6/2003 | Crandall et al. |
| 2003/0135214 A1 | 7/2003 | Fetto et al. |
| 2003/0149431 A1 | 8/2003 | Varieur |
| 2003/0187440 A1 | 10/2003 | Richelsoph et al. |
| 2003/0187442 A1 | 10/2003 | Richelsoph et al. |
| 2003/0204189 A1 | 10/2003 | Cragg |
| 2003/0208203 A1 | 11/2003 | Lim et al. |
| 2003/0220641 A1 | 11/2003 | Thelen et al. |
| 2003/0229345 A1 | 12/2003 | Stahurski |
| 2003/0229347 A1 | 12/2003 | Sherman et al. |
| 2004/0015169 A1 | 1/2004 | Gause |
| 2004/0030336 A1 | 2/2004 | Khanna |
| 2004/0034350 A1 | 2/2004 | St. Onge et al. |
| 2004/0039384 A1 | 2/2004 | Boehm, Jr. et al. |
| 2004/0039387 A1 | 2/2004 | Gause et al. |
| 2004/0049197 A1 | 3/2004 | Barbera Alacreu |
| 2004/0068319 A1 | 4/2004 | Cordaro |
| 2004/0092934 A1 | 5/2004 | Howland |
| 2004/0097935 A1 | 5/2004 | Richelsoph et al. |
| 2004/0102775 A1 | 5/2004 | Huebner |
| 2004/0122442 A1 | 6/2004 | Lewis |
| 2004/0127897 A1 | 7/2004 | Freid et al. |
| 2004/0127903 A1 | 7/2004 | Schlapfer et al. |
| 2004/0133207 A1 | 7/2004 | Abdou |
| 2004/0138660 A1 | 7/2004 | Serhan |
| 2004/0153070 A1 | 8/2004 | Barker et al. |
| 2004/0158247 A1 | 8/2004 | Sitiso et al. |
| 2004/0204711 A1 | 10/2004 | Jackson |
| 2004/0215190 A1 | 10/2004 | Nguyen et al. |
| 2004/0220570 A1 | 11/2004 | Frigg |
| 2004/0243126 A1 | 12/2004 | Carbone et al. |
| 2004/0254579 A1 | 12/2004 | Buhren et al. |
| 2004/0260284 A1 | 12/2004 | Parker |
| 2004/0260297 A1 | 12/2004 | Padget et al. |
| 2005/0010214 A1 | 1/2005 | Tassin |
| 2005/0033298 A1 | 2/2005 | Hawkes et al. |
| 2005/0075633 A1 | 4/2005 | Ross |
| 2005/0085813 A1 | 4/2005 | Spitler et al. |
| 2005/0090827 A1 | 4/2005 | Gedebou |
| 2005/0096657 A1 | 5/2005 | Autericque et al. |
| 2005/0119659 A1 | 6/2005 | Pfefferle et al. |
| 2005/0124994 A1 | 6/2005 | Berger et al. |
| 2005/0131408 A1 | 6/2005 | Sicvol et al. |
| 2005/0187548 A1 | 8/2005 | Butler et al. |
| 2005/0192575 A1 | 9/2005 | Pacheco |
| 2005/0216003 A1 | 9/2005 | Biedermann et al. |
| 2005/0222570 A1 | 10/2005 | Jackson |
| 2005/0228379 A1 | 10/2005 | Jackson |
| 2005/0251138 A1 | 11/2005 | Boris et al. |
| 2005/0261687 A1 | 11/2005 | Garamszegi et al. |

| | | |
|---|---|---|
| 2005/0277919 A1 | 12/2005 | Slivka et al. |
| 2005/0277922 A1 | 12/2005 | Trieu et al. |
| 2005/0277925 A1 | 12/2005 | Mujwid |
| 2005/0283157 A1 | 12/2005 | Coates et al. |
| 2006/0004360 A1 | 1/2006 | Kramer et al. |
| 2006/0025771 A1 | 2/2006 | Jackson |
| 2006/0030851 A1 | 2/2006 | Bray et al. |
| 2006/0036240 A1 | 2/2006 | Colleran et al. |
| 2006/0036252 A1 | 2/2006 | Baynham et al. |
| 2006/0047282 A1 | 3/2006 | Gordon |
| 2006/0064092 A1 | 3/2006 | Howland |
| 2006/0079892 A1 | 4/2006 | Roychowdhury et al. |
| 2006/0116680 A1 | 6/2006 | Kugler et al. |
| 2006/0122602 A1 | 6/2006 | Konieczynski et al. |
| 2006/0142767 A1 | 6/2006 | Green et al. |
| 2006/0155283 A1 | 7/2006 | Doherty et al. |
| 2006/0167454 A1 | 7/2006 | Ludwig et al. |
| 2006/0195086 A1 | 8/2006 | Sybert |
| 2006/0195096 A1 | 8/2006 | Lee et al. |
| 2006/0200129 A1 | 9/2006 | Denti |
| 2006/0200131 A1 | 9/2006 | Chao et al. |
| 2006/0229614 A1 | 10/2006 | Foley et al. |
| 2006/0241595 A1 | 10/2006 | Molz, IV et al. |
| 2006/0247650 A1 | 11/2006 | Yerby et al. |
| 2006/0282075 A1 | 12/2006 | Labrom et al. |
| 2006/0282076 A1 | 12/2006 | Labrom |
| 2006/0282077 A1 | 12/2006 | Labrom |
| 2006/0282078 A1 | 12/2006 | Labrom |
| 2006/0282079 A1 | 12/2006 | Labrom |
| 2007/0010818 A1 | 1/2007 | Stone et al. |
| 2007/0016195 A1 | 1/2007 | Winslow et al. |
| 2007/0016200 A1 | 1/2007 | Jackson |
| 2007/0016219 A1 | 1/2007 | Levine |
| 2007/0043358 A1 | 2/2007 | Molz, IV et al. |
| 2007/0049931 A1 | 3/2007 | Justis et al. |
| 2007/0055242 A1 | 3/2007 | Bailly |
| 2007/0073405 A1 | 3/2007 | Verhulst et al. |
| 2007/0083202 A1 | 4/2007 | Eli Running et al. |
| 2007/0083203 A1 | 4/2007 | Ribeiro |
| 2007/0093817 A1 | 4/2007 | Barrus et al. |
| 2007/0093821 A1 | 4/2007 | Freudiger |
| 2007/0093904 A1 | 4/2007 | Biedermann et al. |
| 2007/0162044 A1 | 7/2007 | Marino |
| 2009/0062914 A1 | 3/2009 | Marino |
| 2009/0105716 A1 | 4/2009 | Barrus |
| 2009/0105769 A1 | 4/2009 | Rock et al. |

FOREIGN PATENT DOCUMENTS

| | | |
|---|---|---|
| WO | WO 00/62684 | 10/2000 |
| WO | WO 01/41681 | 6/2001 |
| WO | WO 2006/116606 | 11/2006 |
| WO | WO 2007/062132 | 5/2007 |

* cited by examiner

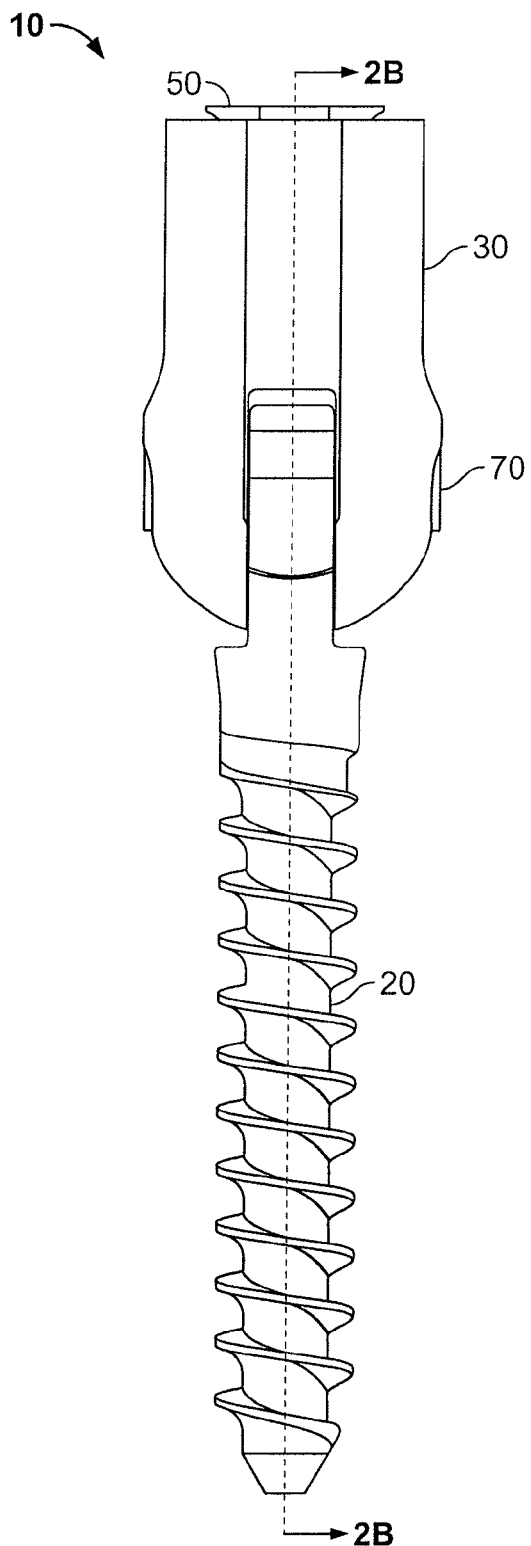
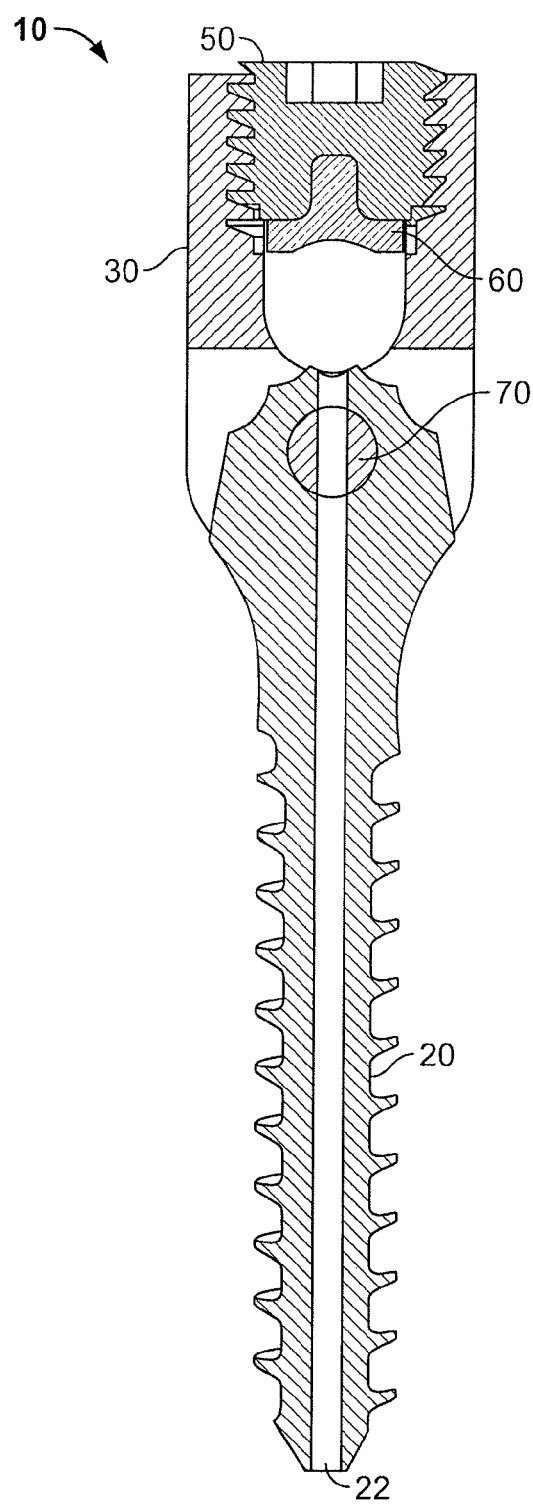
FIG. 2A  FIG. 2B

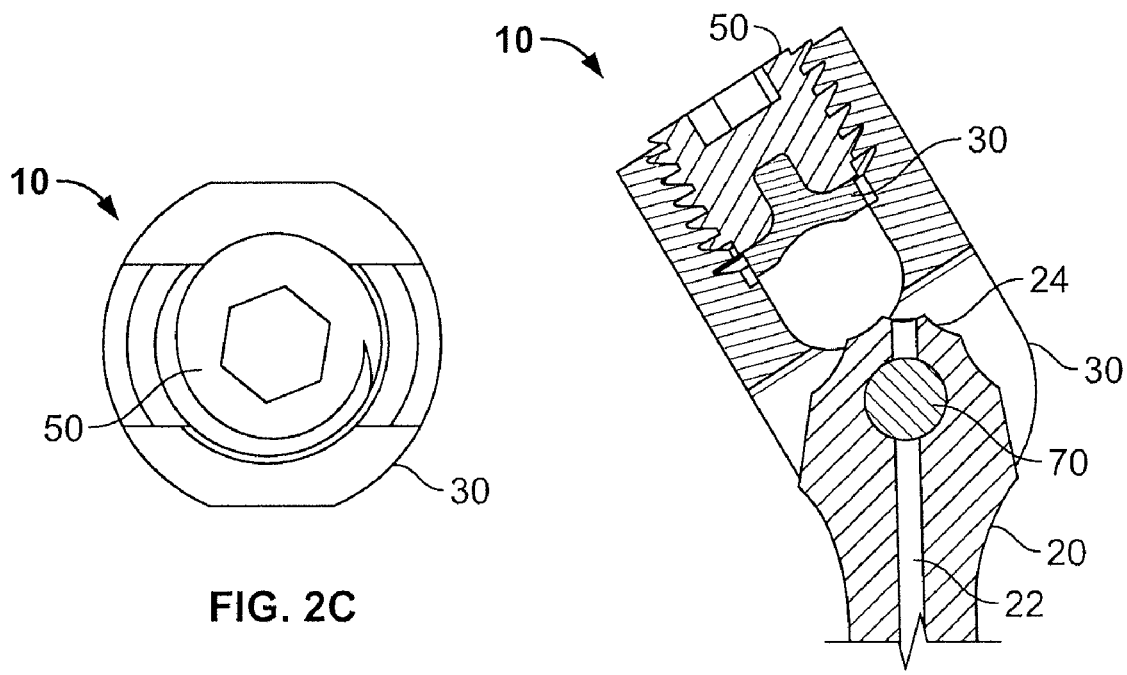
FIG. 2C
FIG. 4A
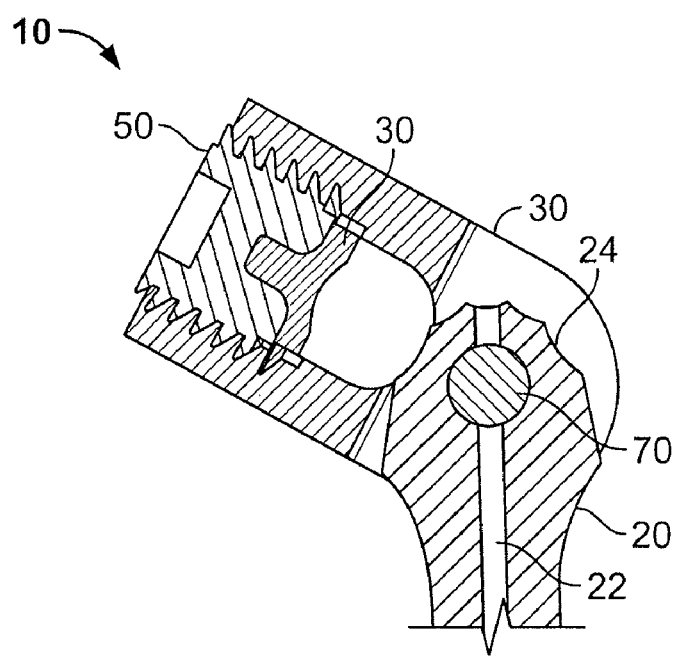
FIG. 4B

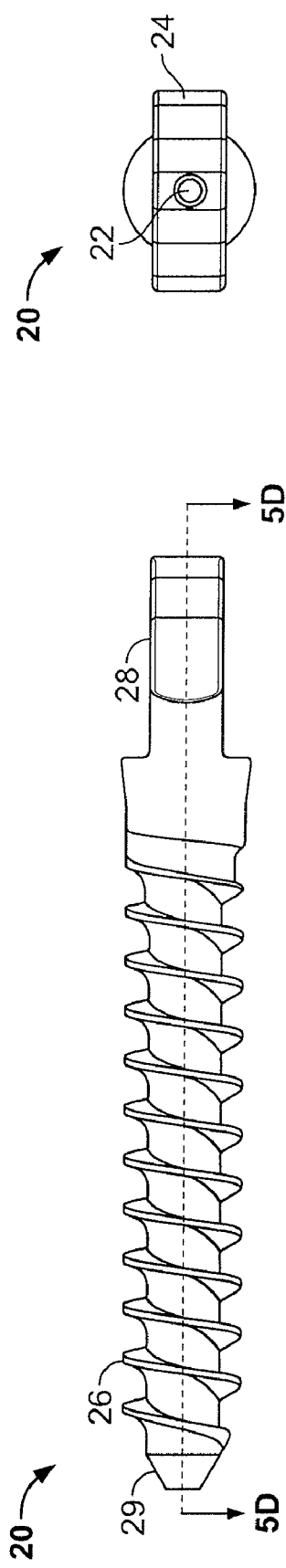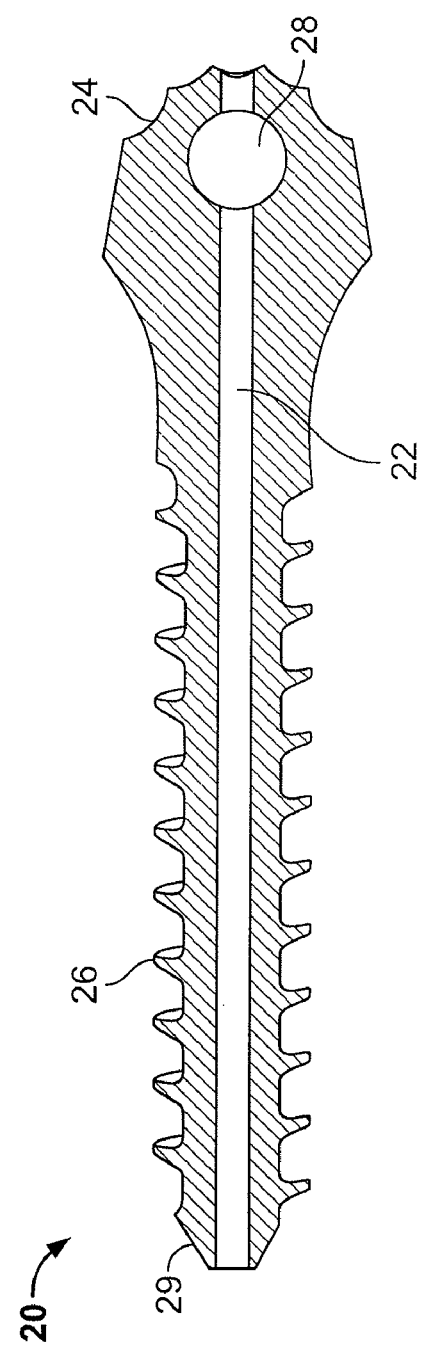
FIG. 5C
FIG. 5B
FIG. 5D

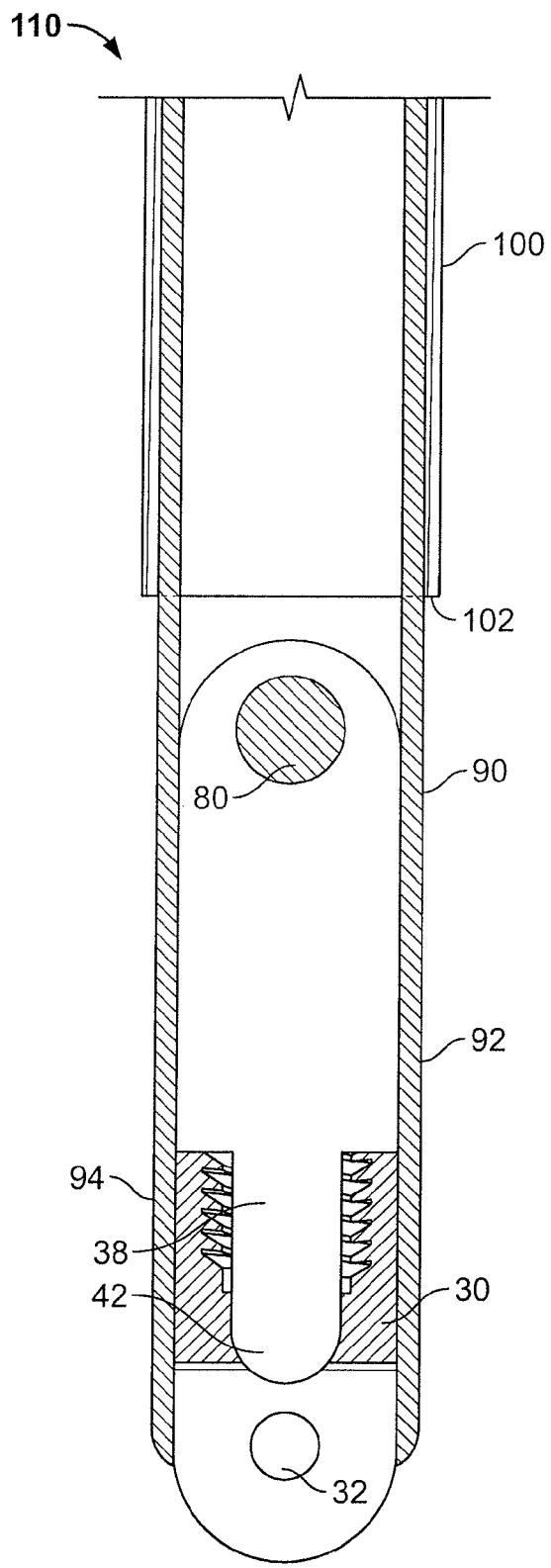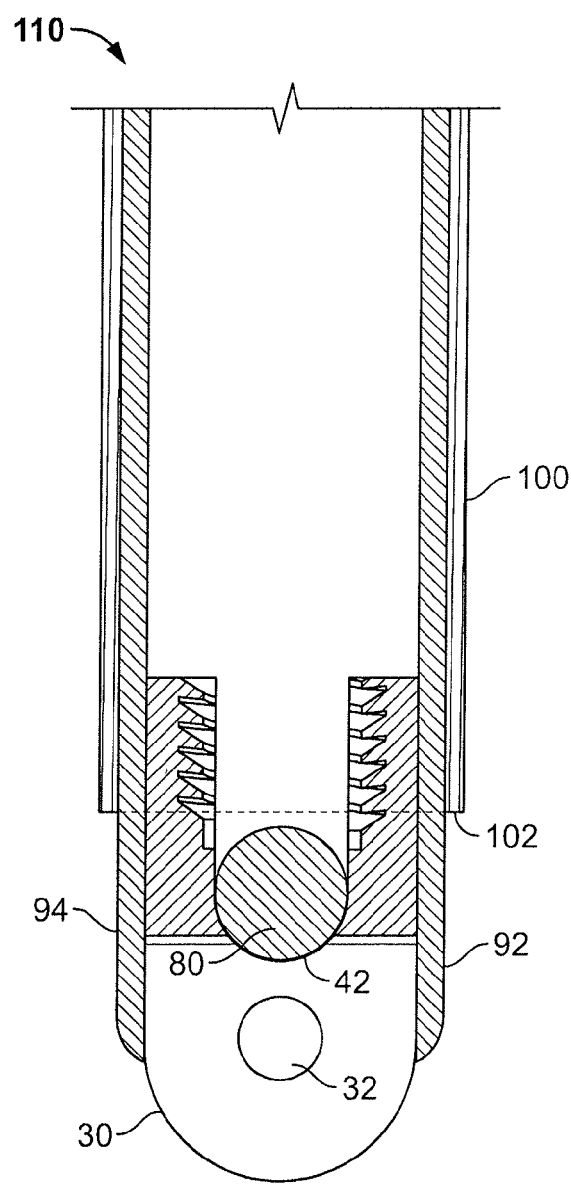
FIG. 11A  FIG. 11B

MONO-PLANAR PEDICLE SCREW METHOD, SYSTEM AND KIT

RELATED APPLICATIONS

This application is a continuation of U.S. patent application Ser. No. 11/916,277 filed on Nov. 30, 2007, now U.S. Pat. No. 7,780,706, entitled, "Mono-planar Pedicle Screw Method, System and Kit," which is a national stage application of and claims the benefit of PCT/US2006/016042 filed on Apr. 27, 2006, which claims the benefit of U.S. Provisional Patent Application No. 60/675,742, filed Apr. 27, 2005, and entitled "Uni-axial Pedicle Screw Construct with Set Screw and Percutaneous Rod Linkage Features Method, System, and Kit". Priority of the aforementioned filing dates is hereby claimed and the entire disclosures of which are hereby incorporated by reference.

BACKGROUND

I. Field of Invention

The invention relates generally to orthopedic boney fixation systems and methods, and more particularly, to facet fixation systems and methods.

II. Description of Related Art

Some pedicle screw systems include a bone screw coupled to a rod receiving component or head. In these systems the screw may be moveable angularly relative to the rod receiving head prior to rod lock down. Such systems typically provide limited angular movement between the screw and rod receiving head. It is desirable to provide an easy to use and install pedicle screw system and a system that enables less limited angular movement between the screw and the rod receiving head. The present invention provides such a system and method.

SUMMARY

The present invention includes a pedicle screw assembly (10) that includes a cannulated pedicle screw (20) having a scalloped shank (24), a swivel top head 30 having inclined female threads (44) in a left and right arm (34, 36) to prevent splaying, a set screw (50) having mating male threads 52, a rod conforming washer (60) that is rotatably coupled to the set screw (50), the conforming washer including reduced ends to induce a coupled rod (80) to bend. The present invention also includes a rod reduction system including an inner and an outer cannula (90, 100), the inner cannula (90) including a left and right arm (92, 94) that engage the swivel top head's (30) left and right arm (34, 36) and the outer cannula (100) dimensioned to securely slide over the inner cannula (90) to reduce the rod (80) into the swivel top head's (30) rod receiving area (38).

In an embodiment the screw shank includes a predetermined number of scallops where each scallop is shaped to engage a rod. In this embodiment the position of the swivel top head to the screw has a predetermined number of locations based on the number of scallops.

BRIEF DESCRIPTION OF THE DRAWINGS

The features, objects, and advantages of the present invention will become more apparent from the detailed description set forth below when taken in conjunction with the drawings in which like reference characters identify correspondingly throughout and wherein:

FIG. 2A is a side view of the pedicle screw assembly shown hi FIG. 1A.

FIG. 2B is a sectional view of the pedicle screw assembly shown in FIG. 2A along line AA.

FIG. 2C is a top view of the pedicle screw assembly shown in FIG. 1A.

FIG. 4A is a partial section view of the pedicle screw assembly shown in FIG. 1A showing swivel head oriented 30 degrees offset from the longitudinal axis of the screw.

FIG. 4B is a partial section view of the pedicle screw assembly shown in FIG. 1A showing swivel head oriented 60 degrees offset from the longitudinal axis of the screw.

FIG. 5B is a side view of the pedicle screw shown in FIG. 5A.

FIG. 5C is a top view of the pedicle screw shown in FIG. 5A.

FIG. 5D is a sectional view of the pedicle screw shown in FIG. 5B along line AA.

FIG. 11A is a sectional view of a rod reduction system engaged to a swivel head of the assembly shown in FIG. 1A prior to reduction of the rod into the swivel head's rod receiving area.

FIG. 11B is another sectional view of the rod reduction system engaged to a swivel head shown in FIG. 1B after reduction of the rod into the swivel head's rod receiving area.

DETAILED DESCRIPTION

Throughout this description, embodiments and variations are described for the purpose of illustrating uses and implementations of the invention. The illustrative description should be understood as presenting examples of the invention, rather than as limiting the scope of the invention.

Figure 1A:
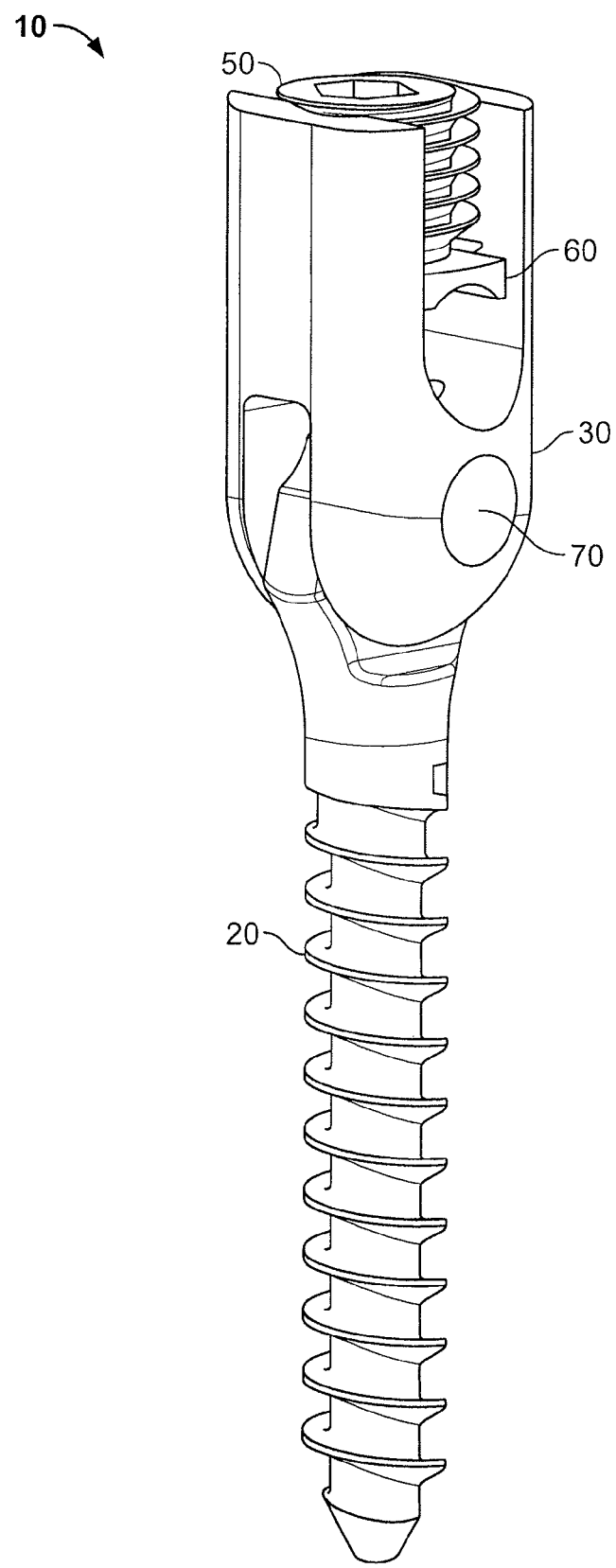
FIG. 1A is an isometric view of a pedicle screw assembly in accordance with the present invention.
Figure 1B:
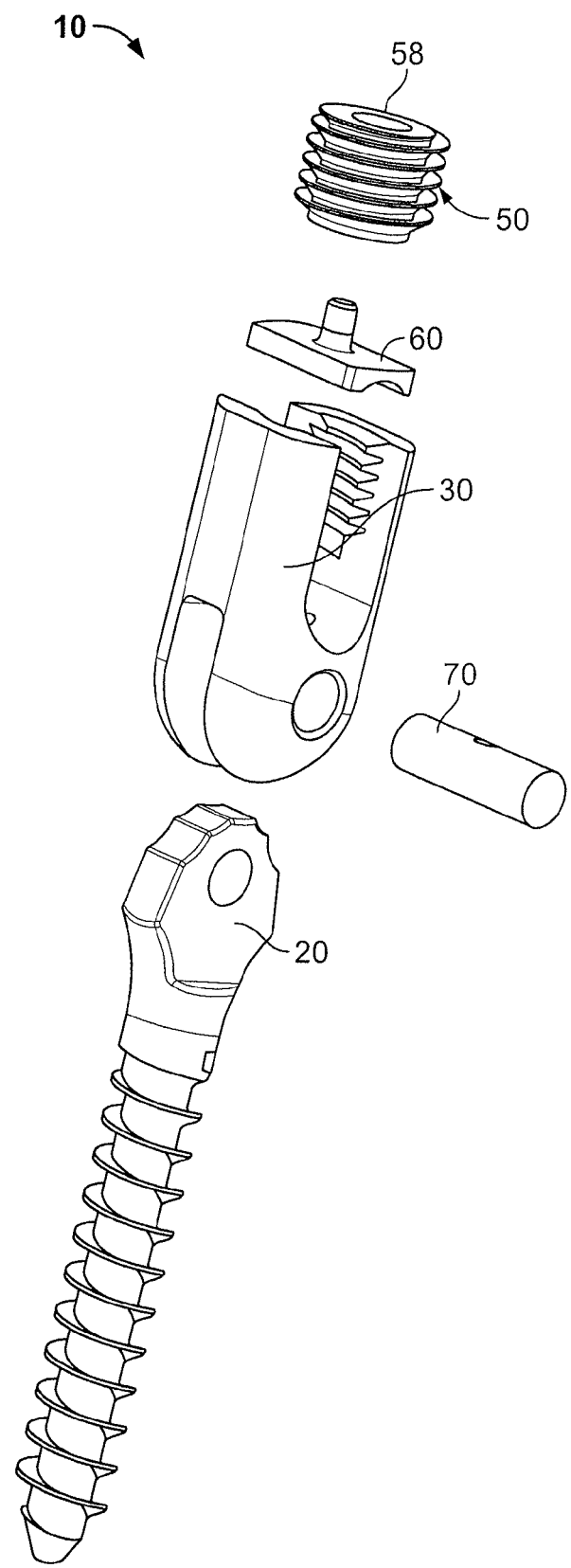
FIG. 1B is an exploded, isometric view of the pedicle screw assembly shown in FIG. 1A.

FIG. 1A is an isometric view of a pedicle screw assembly 10 in accordance with the present invention. FIG. 1B is an exploded, isometric view of the pedicle screw assembly 10 shown in FIG. 1A. The pedicle screw assembly 10 includes a pedicle screw 20, a swivel top head 30, a set screw 50, a conforming washer 60, and a stepped axel 70. The swivel top head 30 is coupled the screw 20 via the stepped axel 70. In one embodiment the conforming washer is rotatably coupled to the set screw 50.

FIG. 2A is a side view of the pedicle screw assembly 10 shown in FIG. 1A, FIG. 2B is a sectional view of the pedicle screw assembly 10 shown in FIG. 2A along line AA, and FIG. 2C is a top view of the pedicle screw assembly 10 shown in FIG. 1A. As shown in FIG. 2B, the pedicle screw 20 may be cannulated 22. In a process employing the pedicle screw 20, a guide wire (not shown) may first be securely placed in a pedicle. Then the pedicle screw assembly 10 without the set screw 50 and conforming washer 60 pair may be inserted over the guide wire to the pedicle via the cannulation 22. The screw 20 may then be advanced into the pedicle boney process and the guide wire removed from the pedicle bony process via the cannulation 22.

Figure 3A:
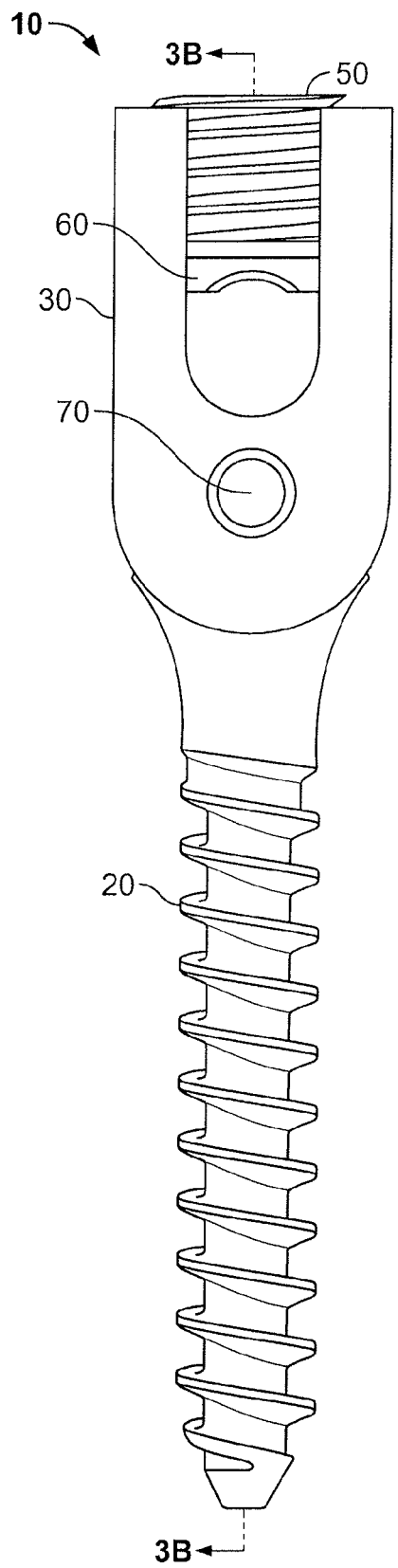
FIG. 3A is a front view of the pedicle screw assembly shown in FIG. 1A.
Figure 3B:
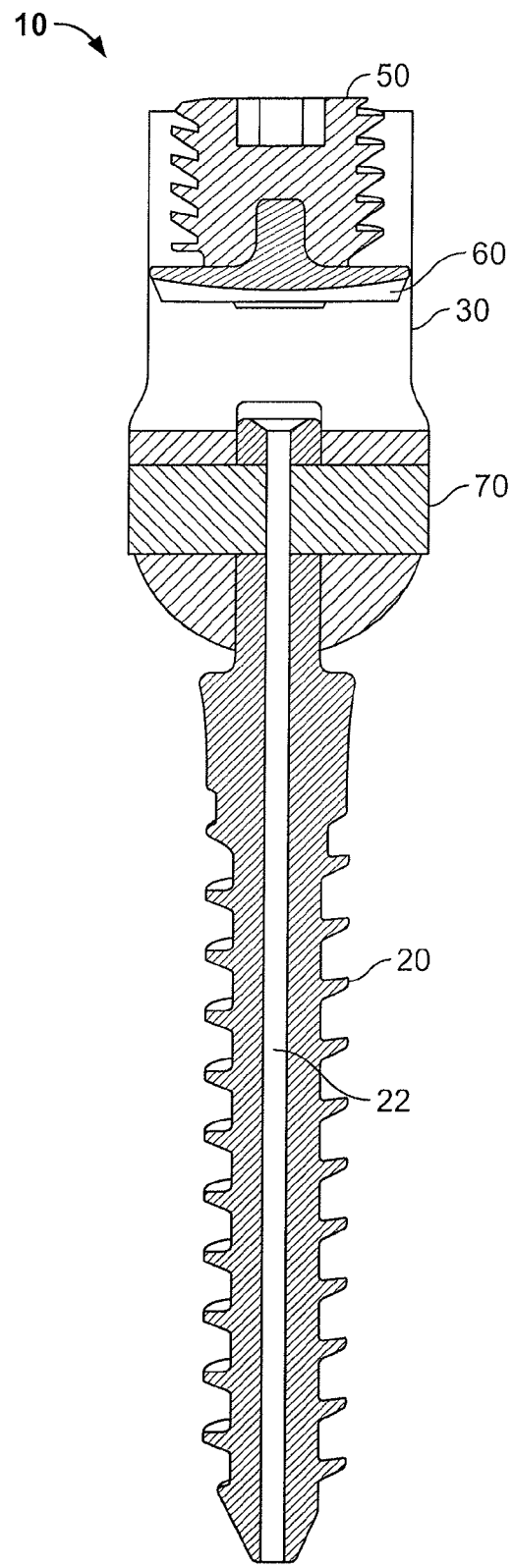
FIG. 3B is a sectional view of the pedicle screw assembly shown in FIG. 3A along line BB.

FIG. 3A is a front view of the pedicle screw assembly 10 shown in FIG. 1A and FIG. 3B is a sectional view of the pedicle screw assembly shown in FIG. 3A along line BB. As shown in FIG. 3B the stepped axel 70 extends through the pedicle screw 20 into the swivel top head 30. FIG. 3B also shows the conforming washing integrated within the set screw 50. As noted in one embodiment, the conforming washer 60 is rotatably integrated or coupled to the set screw 50.

FIG. 4A is a partial sectional view of the pedicle screw assembly 10 shown in FIG. 1A showing the swivel head 30 oriented 30 degrees offset from the longitudinal axis of the screw 20 along a single plane, mono-planar relative to the screw axis. FIG. 4B is a partial sectional view of the pedicle screw assembly 10 shown in FIG. 1A showing the swivel head 30 oriented 60 degrees offset from the longitudinal axis of the screw 20. As shown in FIGS. 4A and 4B, the pedicle screw 20 may have a scalloped shank 24 having a predetermined number of scallops. The scallops may have a concave shape to engage a rounded rod 80 (see FIG. 11A). In other embodiments the scallops may have different shapes as a function of the rod shape 80. After the screw 20 is advanced into a pedicle boney process a rod 80 may be inserted into the swivel head 30. Once the desired orientation between the screw 20 and swivel head 30 is achieved, the set screw 50 and conforming washer 60 may be inserted to compress the rod 80 against a scallop 24 of the screw 20 to maintain the desired orientation.

Figure 5A:
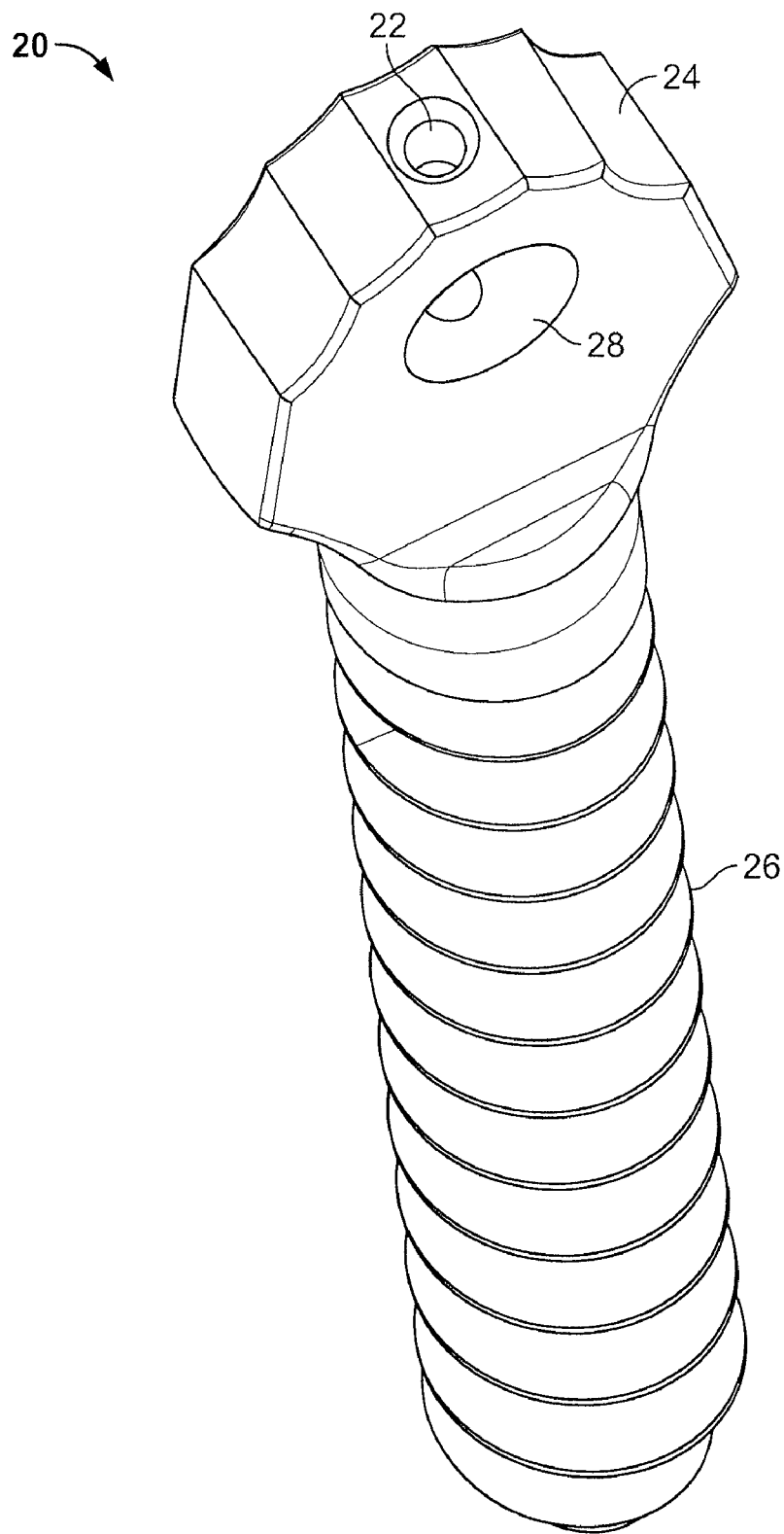
FIG. 5A is an isometric view of a pedicle screw according to an assembly embodiment of the present invention shown in FIG. 1A.

FIG. 5A is an isometric view of a pedicle screw 20 according to an assembly embodiment of the present invention shown in FIG. 1A. FIG. 5B is a side view of the pedicle screw 20 shown in FIG. 5A. FIG. 5C is a top view of the pedicle screw 20 shown in FIG. 5A. FIG. 5D is a sectional view of the pedicle screw 20 shown in FIG. 5B along line AA. The pedicle screw 20 includes screw cannulation 22, plurality of scallops 24, threads, shank axel cannulation 28, and tip 29. As shown in FIG. 5B, the screw 20 tip 29 may be have a chamfer of about 60 degrees. In one process after a guide wire is securely inserted into a pedicle boney process a cannulated screw tap (not shown) may be inserted over the guide wire. The cannulated screw tap may then be used to create a tap within the pedicle boney process. The screw 20 includes the chamfered tip 29 to aid insertion into the tapped pedicle boney process, m one embodiment the screw 20 is inserted in a minimally invasive process so a practitioner may not be able to visual orient the screw within the formed pedicle tap.

Figure 5E:
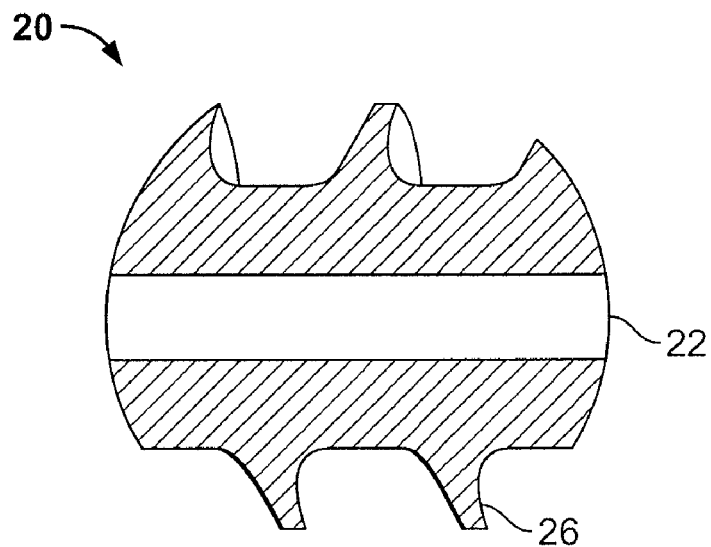
FIG. 5E is a detailed view of the segment B of the sectional pedicle screw shown in FIG. 5D.

FIGS. 5B, 5C, and 5D also include some dimensions. It is noted that the pedicle screw assembly 10 may work with screws 20 having different length and radii as a function of patient anatomy, in addition, the scallop dimensions and shape may vary as a function of the rod 80 to be employed with the pedicle screw assembly, in one embodiment the pedicle screw assembly consists primarily of titanium. FIG. 5E is a detailed view of the segment B (threads 26) of the sectional pedicle screw 20 shown in FIG. 5D. The thread pattern 26 is one embodiment in accordance with the present invention and the dimensions are also according to one embodiment in accordance with the present invention.

Figure 6A:
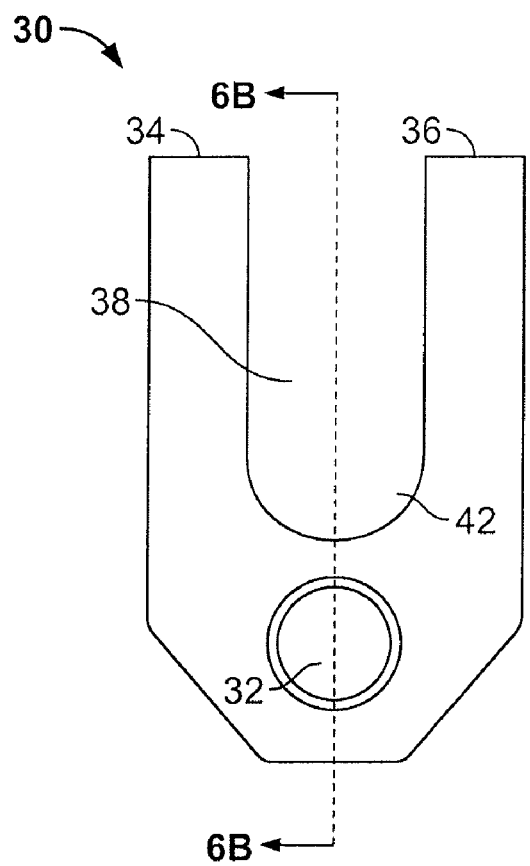
FIG. 6A is a side view of a swivel top head according to an assembly embodiment of the present invention shown in FIG. 1A.
Figure 6B:
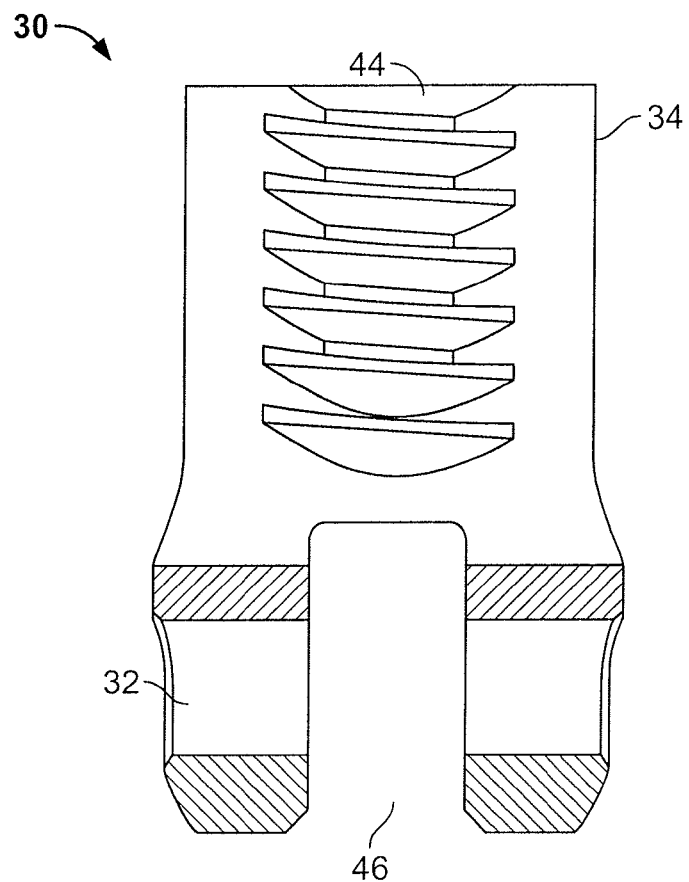
FIG. 6B is a sectional view of the swivel top head shown in FIG. 6A along line AA.
Figure 6C:
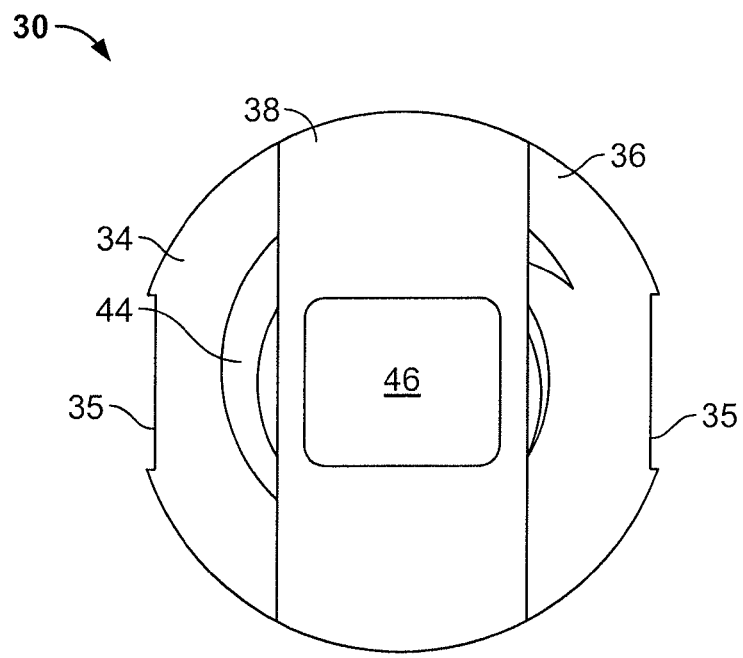
FIG. 6C is a top view of the swivel top head shown in FIG. 6A.

FIG. 6A is a side view of a swivel top head 30 according to an assembly embodiment of the present invention shown in FIG. 1A. FIG. 6B is a sectional view of the swivel top head 30 shown in FIG. 6A along line AA. FIG. 6C is a top view of the swivel top head 30 shown in FIG. 6A. The swivel top head 30 includes a head axel cannulation 32, left head arm 34, right head arm 36, head receiving channel 38, head rod seating area 42, female thread 44, and screw 20 shank receiving area 46. The left head arm 34 and right head arm 36 each include the female thread 44. FIGS. 6B and 6C include dimensions for one embodiment of a swivel top head 30 in accordance with the present invention.

Figure 7A:
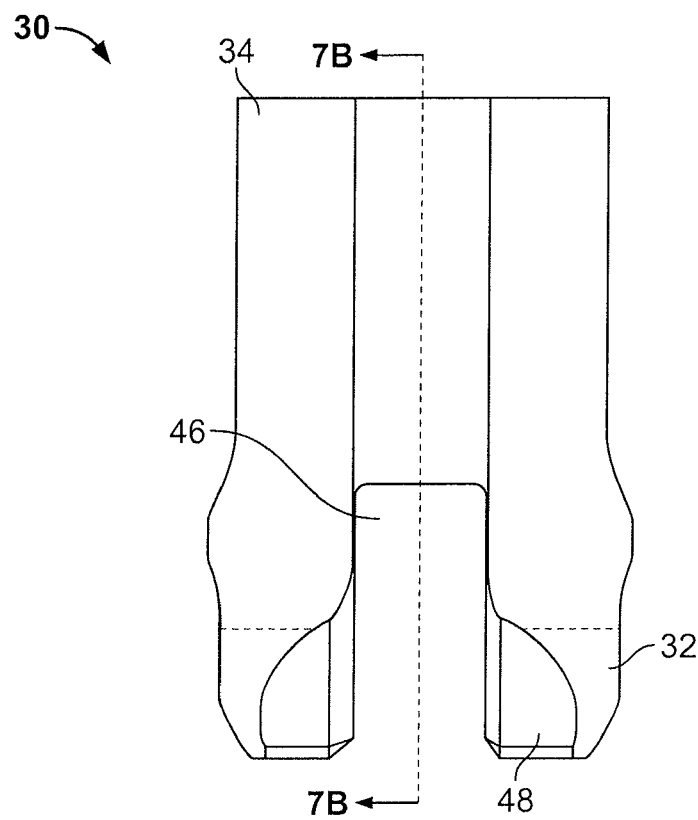
FIG. 7A is a front view of a swivel top head according to an assembly embodiment of the present invention shown in FIG. 1A.
Figure 7B:
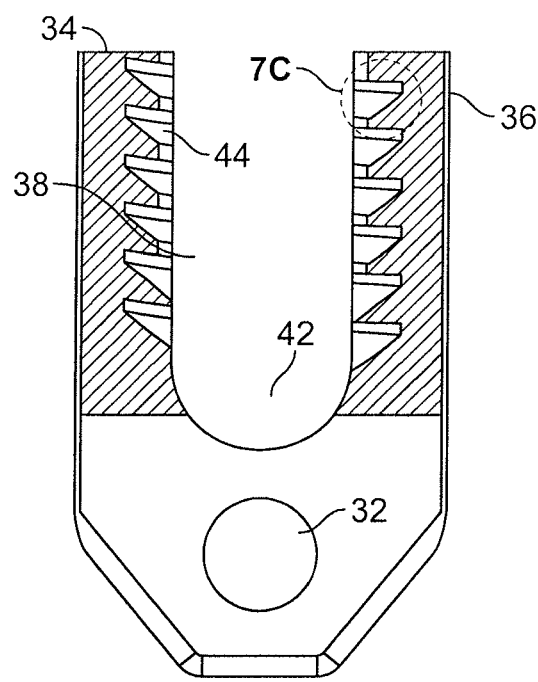
FIG. 7B is a sectional view of the swivel top head shown in FIG. 7A along line BB.

FIG. 7A is a front view of a swivel top head 30 according to an assembly embodiment 10 of the present invention shown in FIG. 1A and FIG. 7B is a sectional view of the swivel top head 30 shown in FIG. 7A along line BB. FIGS. 7A and 7B include dimensions for one embodiment of a swivel top head 30 in accordance with the present invention. As shown in FIG. 7A the swivel top head 30 includes a head axel cannulation offset 48.

Figure 7C:
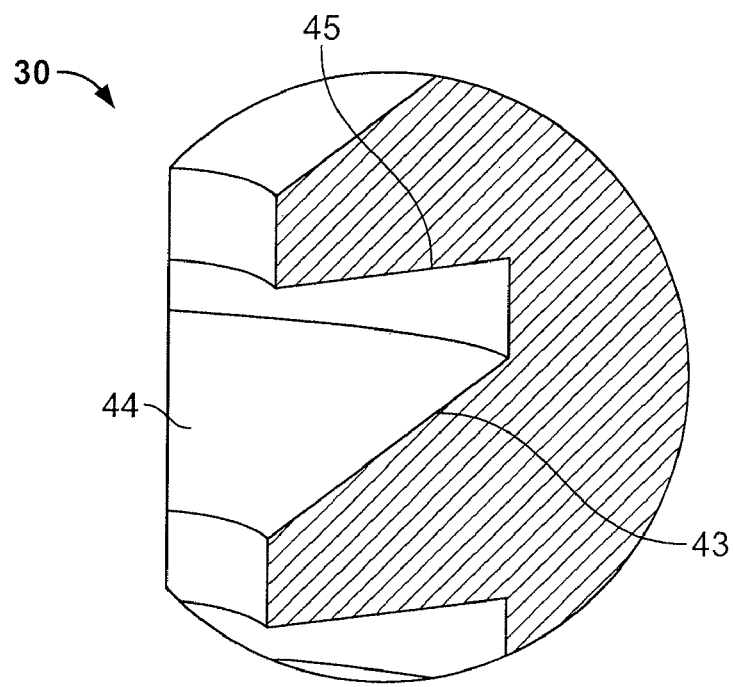
FIG. 7C is a sectional view of the detail area C of swivel top head shown in FIG. 7B.

FIG. 7C is a sectional view of the detail area C of swivel top head 30 female thread 44 shown in FIG. 7B. The thread 44 includes a female thread lower rail 43 and a female thread upper rail. FIG. 7C includes dimensions for one embodiment of a female thread 44 for a swivel top head 30 in accordance with the present invention. As shown in FIG. 7C, the thread rails 43 and 45 are upwardly inclined. In a process where the set screw 50 is inserted into the left and right arms, the thread pattern 44 will prevent splaying of the arms 34 and 36.

Figure 8A:
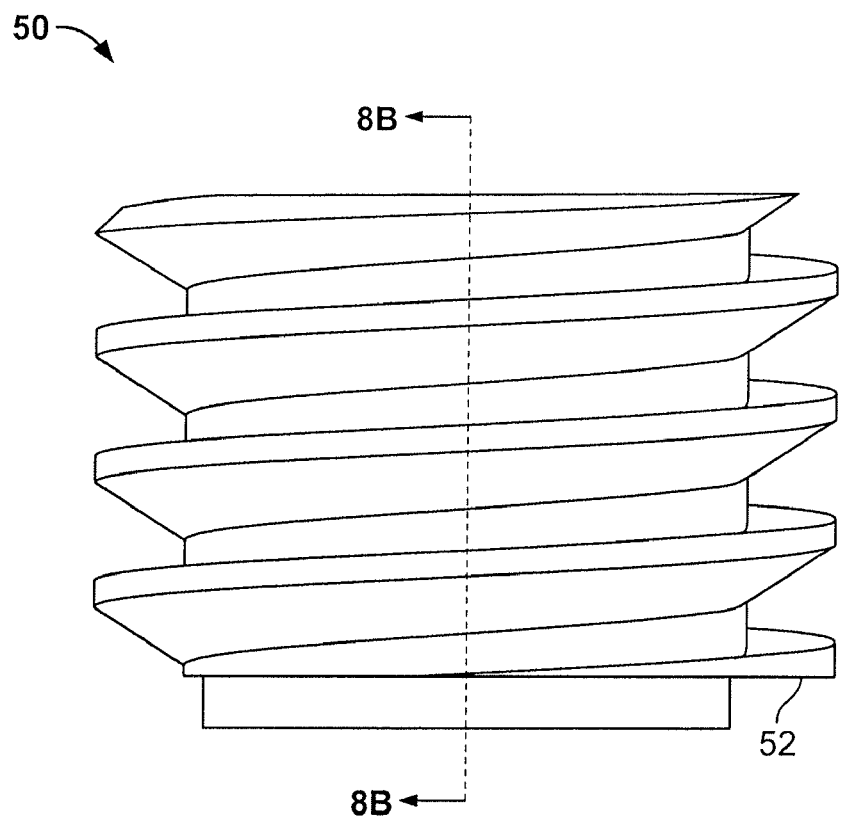
FIG. 8A is a side view of a set screw according to an assembly embodiment of the present invention shown in FIG. 1A.
Figure 8B:
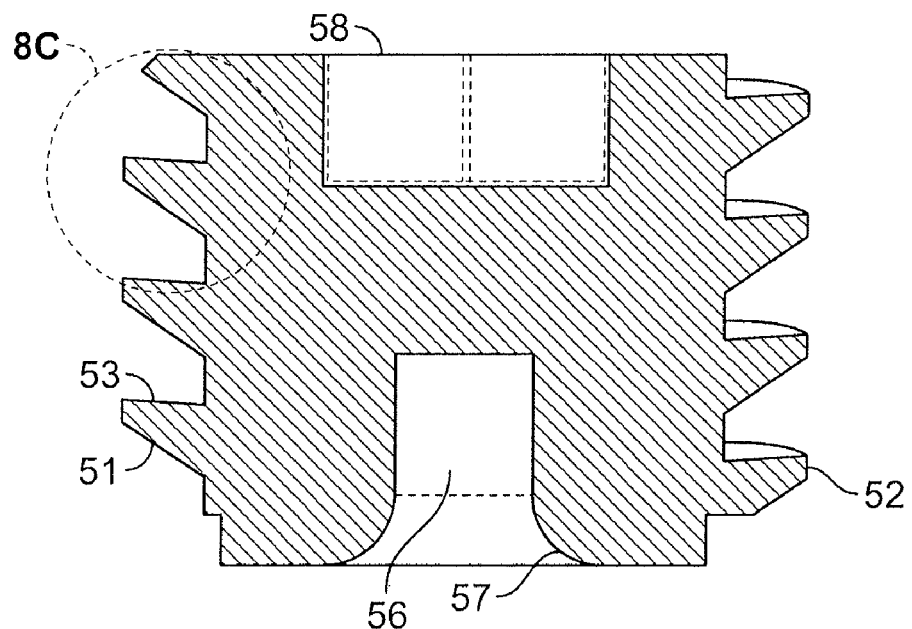
FIG. 8B is a sectional view of the set screw shown in FIG. 8A along line AA.
Figure 8C:
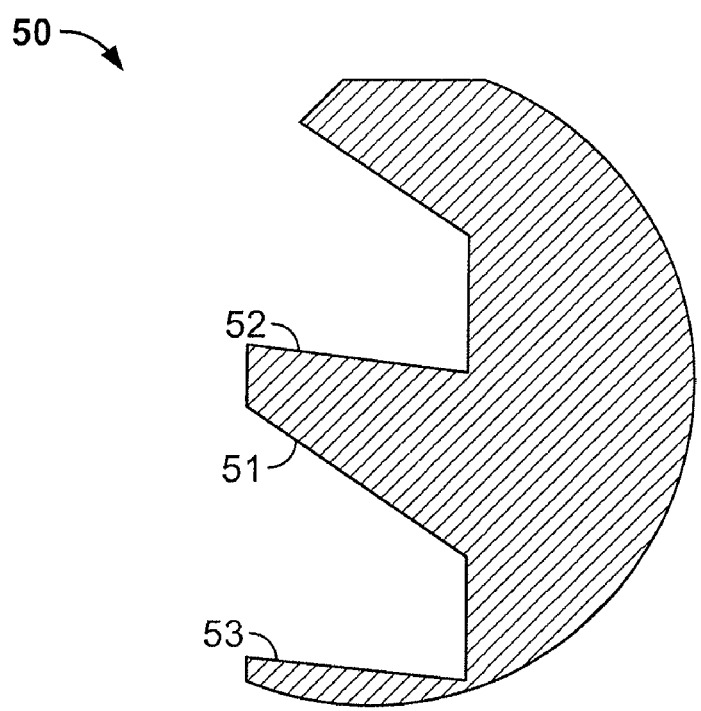
FIG. 8C is a sectional view of the detail area B of the set screw shown in FIG. 8B.
Figure 8D:
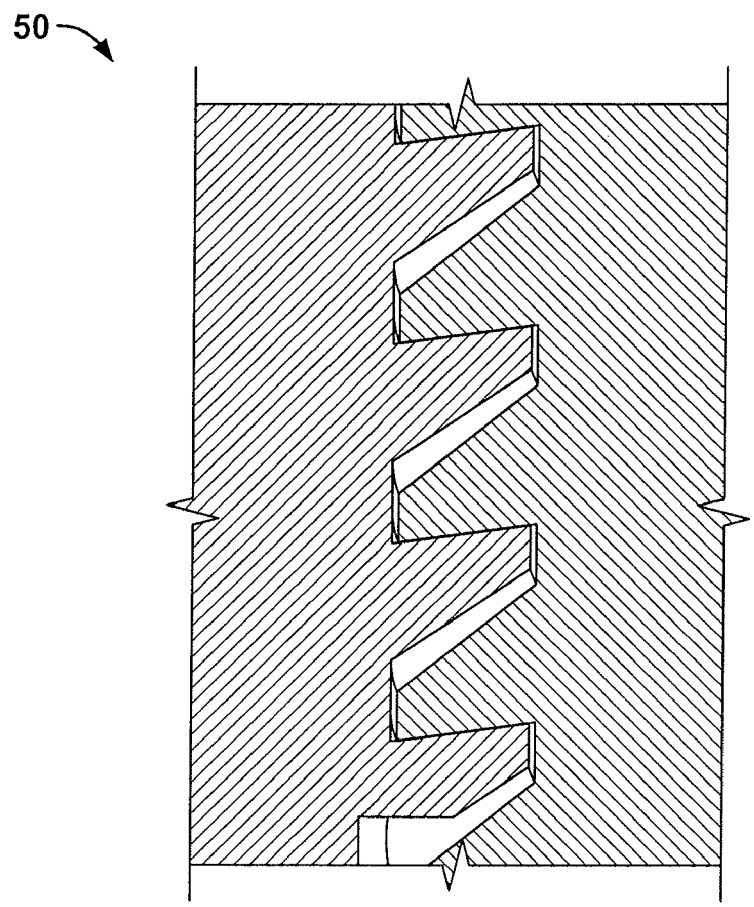
FIG. 8D is a partial, sectional view of the set screw shown in FIG. 8A.
Figure 8E:
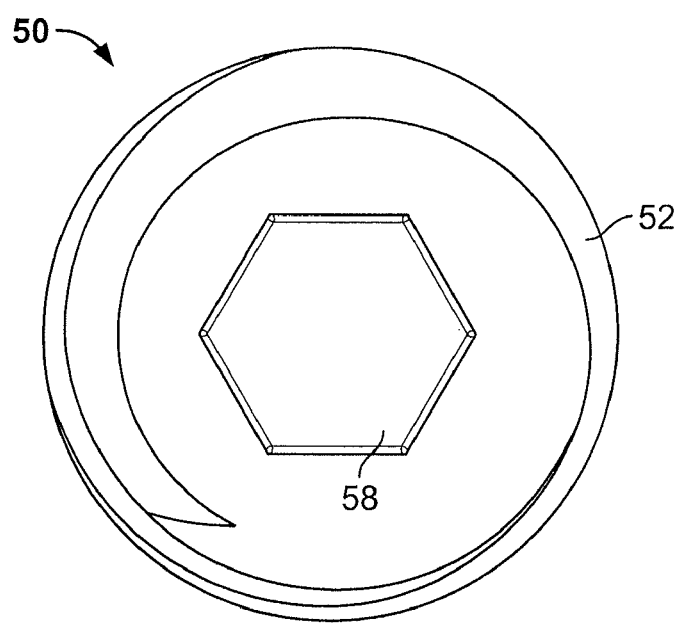
FIG. 8E is a top view of the set screw shown in FIG. 8A.

FIG. 8A is a side view of a set screw 50 according to an assembly embodiment of the present invention shown in FIG. 1A. FIG. 8B is a sectional view of the set screw 50 shown in FIG. 8A along line AA. FIG. 8C is a sectional view of the detail area B of the set screw 50 shown in FIG. 8B. FIG. 8D is a partial, sectional view of the set screw 50 shown in FIG. 8A. FIG. 8E is a top view of the set screw 50 shown in FIG. 8A. FIGS. 8B and 8C include dimensions for one embodiment of a set screw 50 in accordance with the present invention. The set screw 50 includes a thread 52, conforming washer head receiving chamber 56, and set screw hexagonal key 58. The male thread 52 includes lower edge 51 and upper edge 54. The thread 52 is dimensioned to match with the female thread 44 to engage the arms 34 and 36 and prevent or limit splaying of the arms 34 and 36. The receiving chamber 56 may also include a receiving chamber edge 57.

Figure 9A:
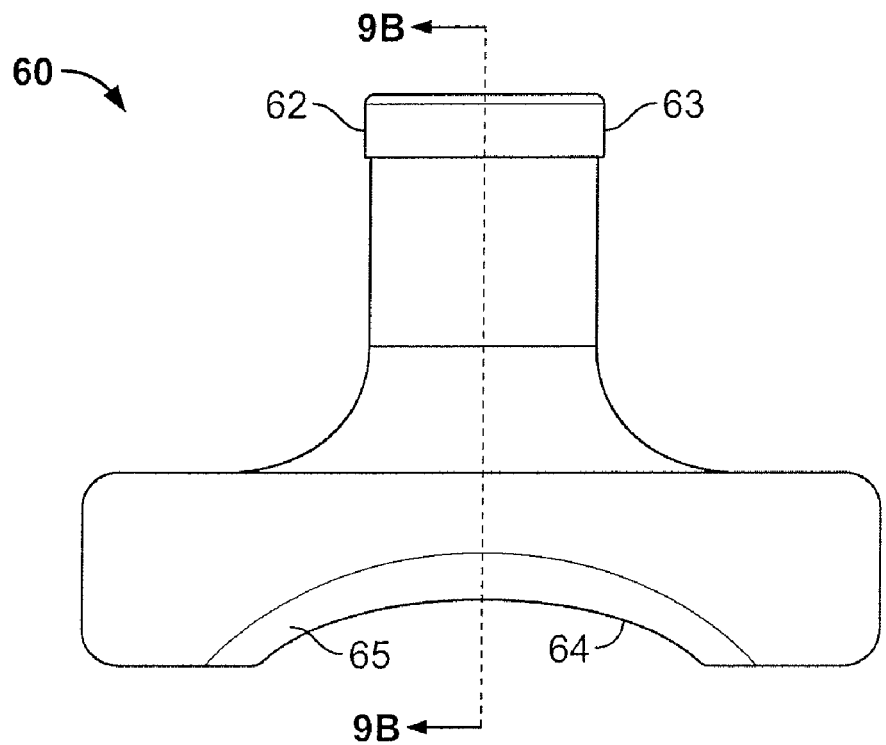
FIG. 9A is an end view of a conforming washer according to an assembly embodiment of the present invention shown in FIG. 1A.
Figure 9B:
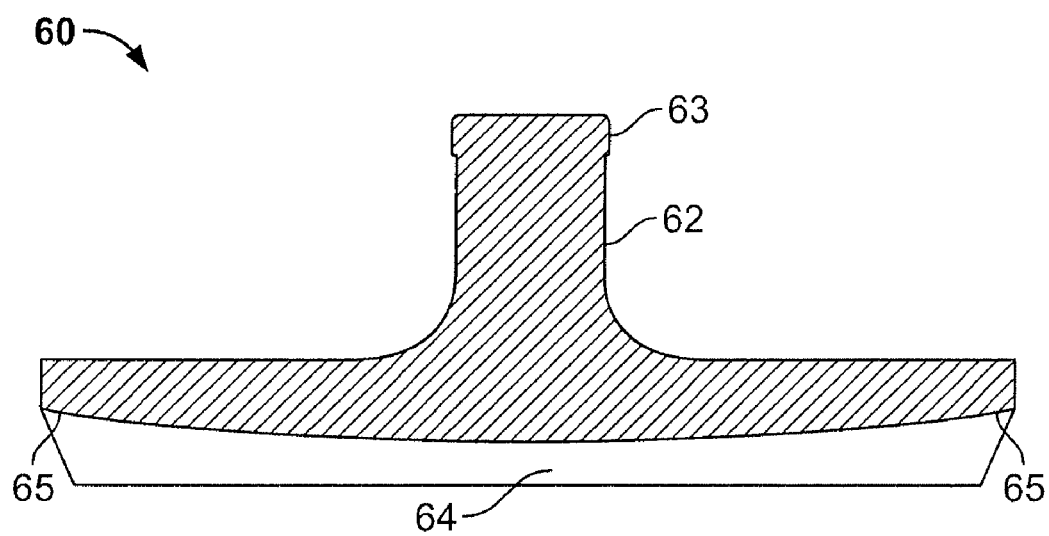
FIG. 9B is a sectional view of the conforming washer shown in FIG. 9A along line AA.
Figure 9C:
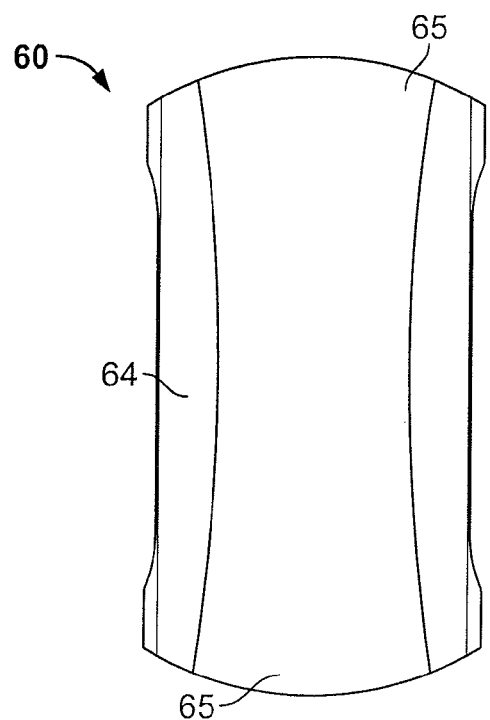
FIG. 9C is a bottom view of the conforming washer shown in FIG. 9A.

FIG. 9A is an end view of a conforming washer 60 according to an assembly embodiment of the present invention shown in FIG. 1A. FIG. 9B is a sectional view of the conforming washer 60 shown in FIG. 9A along line AA. FIG. 9C is a bottom view of the conforming washer 60 shown in FIG. 9A. FIGS. 9A, 9B and 9C include dimensions for one embodiment of a conforming washer 60 in accordance with the present invention. The conforming washer 60 includes a washer head 62, washer head enlarged cap 63, rod conforming section 64, and rod conforming section reduced ends 65. The washer head 62 is dimensioned to be inserted into the washer head receiving chamber 56. The head enlarged cap 63 is dimensioned to prevent the conforming washer from being disengaged from the set screw 50 upon insertion into the set screw's receiving chamber 56 while enabling the set screw 50 to be rotated independently of the conforming washer 60.

In one embodiment the rod conforming section 64 includes reduced ends 65 that cause the conforming washer 60 bend a rod 80 when the set screw 50 compresses the conforming washer against the rod 80 (and screw shank scallops 24). In one embodiment the conforming washer 60 helps the rod 80 meet the natural lordosis of one or more vertebrae (not shown) that the rod 80 may be coupled thereto via the pedicle screw assembly 10.

Figure 10A:
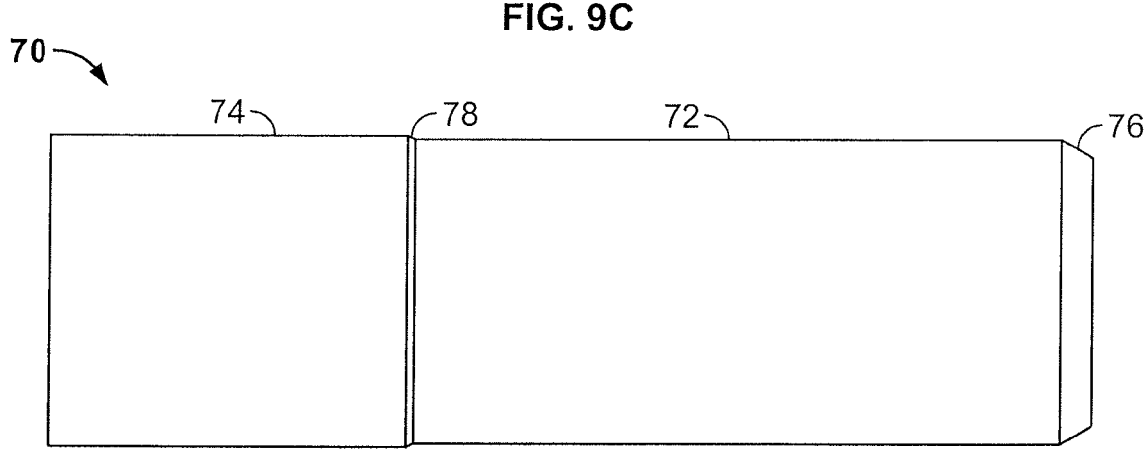
FIG. 10A is a side view of a stepped axel according to an assembly embodiment of the present invention shown in FIG. 1A.
Figure 10B:
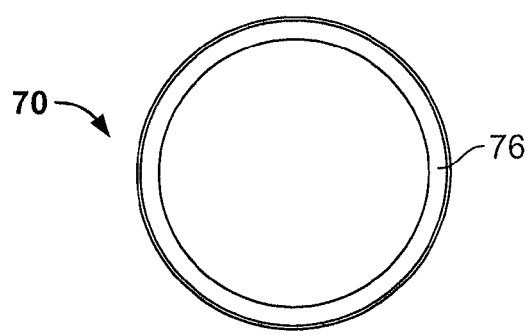
FIG. 10B is an end view of the stepped axel shown in FIG. 10B.

FIG. 10A is a side view of a stepped axel 70 according to an assembly embodiment 10 of the present invention shown in FIG. 1A. FIG. 10B is an end view of the stepped axel 70 shown in FIG. 1B. FIG. 10A includes dimensions for one embodiment of a stepped axel 70 in accordance with the present invention. The stepped axel 70 includes an axel first section 72, an axel second section 74, an axel first section leading edge 76, and an axel second section edge 78. The stepped axel 70 is dimensioned to engage the swivel top head 30 shank receiving area while permitting the pedicle screw 20 to rotate freely thereabout via its shank axel cannulation 28.

FIG. 11A is a sectional view of a rod reduction system engaged to a swivel head 30 of the assembly 10 shown in FIG. 1A prior to reduction of the rod 80 into the swivel head's rod receiving area 38. The rod reduction system includes head engaging cannula 90 and reduction cannula 100. The head engaging cannula 90 includes first arm 94 and a second arm 96. In a process, the cannula 90 may be placed over the rod 80 after the swivel top head 30 with pedicle screw 20 is inserted in a pedicle boney process. The cannula 90's left and right arm 92 and 94 engage the swivel top head's 30 left and right arm 34 and 36. The cannula 90 is open between its arms 92 and 94. In a rod reduction process the cannula is advanced over the cannula 90 to engage the rod 80 and reduce the rod into the swivel top head's 30 rod receiving area 38. In the embodiment, the cannula is dimensioned to slide securely over the cannula 90. FIG. 11B is another sectional view of the rod reduction system where the cannula 90 is engaged to the swivel top head 30 and the rod has been reduced into the swivel top head 30 via the advancement of the cannula over the cannula 90.

While this invention has been described in terms of a best mode for achieving the objectives of the invention, it will be appreciated by those skilled in the wireless communications art that variations may be accomplished in view of these teachings without deviating from the spirit or scope of the present invention.

What is claimed is:

1. A bone anchor assembly, the assembly comprising:
   a screw having a shaft extending from a proximal end to a distal end and a plurality of threads on at least a portion of the shaft; and
   a receiving element comprising:
      a rod-receiving section having a left arm and a right arm extending proximally forming a first channel configured to receive a rod therethrough, wherein the first channel has a first channel plane aligned with a longitudinal axis of the rod extending through the first channel; and
      a screw-receiving section having a first arm and a second arm extending distally forming a second channel configured to receive the screw, wherein the second channel has a second channel plane offset from the first channel plane, and
      wherein the screw is adapted to articulate relative to the receiving element along the second channel plane and is prevented from articulating relative to the receiving element along the first channel plane.

2. The bone anchor assembly of claim 1, wherein the first channel plane is at a right angle to the second channel plane.

3. The bone anchor assembly of claim 1, wherein the screw is adapted to articulate relative to the receiving element only along a plane that intersects and is non-parallel to the first channel plane.

4. The bone anchor assembly of claim 1, wherein the first channel plane defines the sagittal plane or parasagittal plane.

5. The bone anchor assembly of claim 1, further comprising an axle configured to insert through an aperture extending through the screw proximal end and through opposing apertures extending through each of the first arm and second arm of the screw-receiving section to rotatably couple the screw to the receiving element, wherein the screw pivots about the axle.

6. The bone anchor assembly of claim 1, wherein the screw proximal end comprises two approximately flat, opposing walls forming a leading edge and sized to fit within the second channel.

7. The bone anchor assembly of claim 6, wherein the leading edge of the screw proximal end comprises one or more concave surfaces.

8. The bone anchor assembly of claim 7, further comprising the rod extending through the first channel.

9. The bone anchor assembly of claim 8, wherein the receiving element further comprises an internal bore extending between the first channel and the second channel such that the rod engages the leading edge of the screw proximal end.

10. The bone anchor assembly of claim 9, wherein the rod has a substantially uniform convex cross sectional shape complementary to at least one of the one or more concave surfaces.

11. The bone anchor assembly of claim 9, further comprising a compression element adapted to move distally within the internal bore of the receiving element to transmit a compression force on the rod positioned in the first channel toward the proximal end of the screw.

12. The bone anchor assembly of claim 11, wherein the screw is prevented from articulating along the first channel plane both prior to and after compressed association of the rod with the proximal end of the screw.

13. The bone anchor assembly of claim 11, wherein the screw is adapted to articulate relative to the receiving element only along a plane that intersects and is non-parallel to the first channel plane both prior to and after compressed association of the rod with the proximal end of the screw.

14. The bone anchor assembly of claim 11, further comprising a washer dimensioned to fit within the first channel and positioned above the rod extending through the first channel.

15. The bone anchor assembly of claim 14, wherein the washer is rotatably coupled to the compression element.

16. The bone anchor assembly of claim 14, wherein the compression element comprises a chamber within which a proximal portion of the washer resides.

17. The bone anchor assembly of claim 14, wherein the washer has a lower mating surface that interdigitates with at least one surface feature of the rod.

18. The bone anchor assembly of claim 1, further comprising a connecting rod element extending through the rod-receiving section of the receiving element and positioned superior to the proximal end of the screw and further comprising a compressive element positioned within the receiving element superior to the connecting rod, wherein the compressive element and proximal end of the screw each have mating surfaces that interdigitate with complementary mating surfaces of the connecting rod element.

19. The bone anchor assembly of claim 1, wherein the left and right arms further comprise external channels configured for mating with a rod reduction tool.

20. The bone anchor assembly of claim 19, wherein the external channels have undercut features that permit locking of the rod reduction tool within the external channels.

* * * * *